United States Patent
Hong et al.

(10) Patent No.: US 9,029,840 B2
(45) Date of Patent: May 12, 2015

(54) ORGANIC NANOFIBER STRUCTURE BASED ON SELF-ASSEMBLED ORGANOGEL, ORGANIC NANOFIBER TRANSISTOR USING THE SAME, AND METHOD OF MANUFACTURING THE ORGANIC NANOFIBER TRANSISTOR

(71) Applicants: Samsung Electronics Co., Ltd., Suwon-si, Gyeonggi do (KR); Seoul National University R&DB Foundation, Seoul (KR)

(72) Inventors: Jong-in Hong, Seoul (KR); Myoung-chul Um, Seoul (KR); Jung-pyo Hong, Seoul (KR); Seong-hoon Lee, Seoul (KR)

(73) Assignees: Samsung Electronics Co., Ltd. (KR); Seoul National University R&DB Foundation (KR)

( * ) Notice: Subject to any disclaimer, the term of this patent is extended or adjusted under 35 U.S.C. 154(b) by 180 days.

(21) Appl. No.: 13/671,060

(22) Filed: Nov. 7, 2012

(65) Prior Publication Data

US 2013/0069040 A1 Mar. 21, 2013

Related U.S. Application Data

(62) Division of application No. 12/499,310, filed on Jul. 8, 2009, now Pat. No. 8,362,464.

(30) Foreign Application Priority Data

Jul. 9, 2008 (KR) .................. 10-2008-0066471

(51) Int. Cl.

| H01L 51/00 | (2006.01) |
| C07D 495/04 | (2006.01) |
| C07C 15/28 | (2006.01) |
| C07C 15/60 | (2006.01) |
| C07D 409/10 | (2006.01) |
| H01L 51/05 | (2006.01) |

(52) U.S. Cl.
CPC .............. *C07D 495/04* (2013.01); *C07C 15/28* (2013.01); *C07C 15/60* (2013.01); *C07C 2103/24* (2013.01); *C07D 409/10* (2013.01); *H01L 51/0036* (2013.01); *H01L 51/0052* (2013.01); *H01L 51/0058* (2013.01); *H01L 51/0074* (2013.01); *H01L 51/0545* (2013.01); *H01L 51/0508* (2013.01)

(58) Field of Classification Search
USPC ................... 257/40; 252/299.61, 500; 438/99
See application file for complete search history.

(56) References Cited

U.S. PATENT DOCUMENTS

| 2007/0125700 A1 | 6/2007 | Ding et al. |
| 2008/0012006 A1 | 1/2008 | Bailey et al. |
| 2010/0243993 A1 | 9/2010 | Saito et al. |

FOREIGN PATENT DOCUMENTS

| EP | 0388768 A2 | 9/1990 |
| EP | 0388768 A3 | 9/1990 |
| EP | 1090911 A2 | 4/2001 |
| EP | 2083457 A1 | 7/2009 |
| WO | 2005068417 A1 | 7/2005 |
| WO | 2008059817 A1 | 5/2008 |

OTHER PUBLICATIONS

An, Byeong-Kwan, et al., "Strongly Fluorescent Organogel System Comprising Fibrillar Self-Assembly of a Trifluoromethyl-Based Cyanostilbene Derivative," Journal American Chemical Society, 2004, vol. 126, pp. 10232-10233.
Inoue, Daisaku, et al., "Novel Low-Molecular-Weight Gelators Based on Azobenzene Containing L-Amino Acids," Bull. Chem. Soc. Jpn, vol. 78, No. 4, 2005, pp. 721-726.
Jeong, Sunho, et al., "Surface Modification of Novel Organic-Inorganic Hybrid Dielectrics Using Self-Assembled Monolayers," Solid State Phenomena, 2007, vol. 124-126, pp. 295-298.
Li, Xue-Qing, et al., "Functional organogels from highly efficient organogelator based on perylene bisimide semiconductor," Chem. Communications, 2006, pp. 3871-3873.
Um, Myoung-Chul, et al., "High-performance organic semiconductors for thin-film transistors based on 2,6-bis(2-thienylvinyl)anthracene," Journal of Materials Chemistry, 2008, vol. 18, pp. 2234-2239.

*Primary Examiner* — Mark Kopec
*Assistant Examiner* — Haidung Nguyen
(74) *Attorney, Agent, or Firm* — Cantor Colburn LLP

(57) ABSTRACT

An organic nanofiber including a gelled organic semiconductor compound. Also disclosed is an organic semiconductor transistor and a method of manufacturing an organic semiconductor transistor.

6 Claims, 9 Drawing Sheets

(7 of 9 Drawing Sheet(s) Filed in Color)

ORGANIC NANOFIBER STRUCTURE BASED
ON SELF-ASSEMBLED ORGANOGEL,
ORGANIC NANOFIBER TRANSISTOR USING
THE SAME, AND METHOD OF
MANUFACTURING THE ORGANIC
NANOFIBER TRANSISTOR

CROSS-REFERENCE TO RELATED APPLICATIONS

This application is a divisional of U.S. application Ser. No. 12/499,310, filed on Jul. 8, 2009, which claims priority to Korean Patent Application No. 10-2008-0066471, filed on Jul. 9, 2008, and all the benefits accruing therefrom under 35 U.S.C. §119, the contents of which in their entirety are incorporated herein by reference.

BACKGROUND

1. Field

One or more embodiments relate to an organic nanofiber structure based on a self-assembled organogel, an organic nanofiber transistor using the same and a method of manufacturing the organic nanofiber transistor. The organic nanofiber structure and the organic nanofiber transistor can be used to manufacture various flexible high performance electronic devices at low cost.

2. Description of the Related Art

Flat panel display devices, such as liquid crystal display devices and organic electro luminescence display devices, include various thin film transistors ("TFTs") for operating the devices. Recently, much research on manufacturing TFTs using organic semiconductors has been carried out, because TFTs can be simply and inexpensively manufactured and flexible devices can be manufactured using the organic TFTs. In general, organic TFTs include a substrate, a gate electrode, an insulating layer, source and drain electrodes, and a channel layer. The organic TFTs can be classified as a bottom contact organic thin film transistor, in which a channel layer is formed on the source and drain electrodes, or as a top contact organic thin film transistor, in which metal electrodes are formed on a channel layer using mask deposition. Performance of organic thin film transistors may be influenced by field-effect mobility (carrier mobility) and on/off ratio (on/off current ratio). The carrier mobility may vary according to the type of semiconductor, method of forming the thin films (which affects their structure and morphology), the driving voltage and the like.

Recently, much research on organic semiconductor materials for channel layers of organic thin film transistors has been carried out, and characteristics of transistors fabricated using the organic semiconductor materials have been reported. If low molecular weight organic materials such as pentacene are used, transistors may have relatively high carrier mobility and excellent on/off ratio. However, when low molecular weight organic materials are used to form thin films, an expensive vacuum deposition device may be required, and micropatterns may difficult to form. Accordingly, costs for manufacturing organic thin film transistors may be impractical and large area thin films may be difficult to manufacture. Furthermore, stability may be reduced during electrochemical processes.

In addition, when a thin film for an organic thin film transistor is formed using a solution process, the resulting organic thin film transistor may have a disordered intermolecular arrangement and thus well-ordered thin films may be difficult to obtain. As a result, carrier mobility decreases and current leakage on cut off increases, and thus the organic thin film transistor may not be suitable for practical application in an electronic device. Recently, one dimensional ("1D") nano- and micro-structures of organic semiconductors have become of great interest for application in solution processable organic transistors. The self-assembly of a 1D structure of π-conjugated molecules can provide not only well-ordered molecular ordering, but also lack grain boundaries within active layers in organic thin film transistors ("OTFTs"). Very recently, several research groups have developed 1D organic semiconductors from pentacene derivatives, oligoarene, perylene tetracarboxylic diimide ("PTCDI") derivatives, hexabenzocoronene and polythiophene polymers as organic semiconductors via solution phase self-assembly.

SUMMARY

One or more embodiments include an organic nanofiber.

One or more embodiments include an organic nanofiber transistor.

One or more embodiments include a method of manufacturing the organic nanofiber transistor.

Additional aspects, advantages and features are further set forth in the description, which follows.

To achieve the above and/or other aspects, advantages or features, an embodiment includes an organic nanofiber including a gelated organic semiconductor compound.

To achieve the above and/or other aspects, advantages or features, an embodiment includes a method of manufacturing an organic semiconductor transistor, the method includes gelating an organic semiconductor compound, to form a self-assembled structure in an organic solvent; and disposing the self-assembled structure onto a substrate comprising a source electrode and a drain electrode that are insulted from each other, to form a channel layer that electrically connects the source electrode and the drain electrode.

To achieve the above and/or other aspects, advantages or features, an embodiment includes an organic semiconductor transistor including: a substrate; a gate electrode; a source electrode and a drain electrode, which are insulated from the gate electrode; an organic semiconductor layer, which is insulated from the gate electrode and electrically connected to the source and the drain electrodes; and an insulating layer, which insulates the gate electrode from the source and drain electrodes and the organic semiconductor layer, wherein an organic nanofiber including a gelated organic semiconductor compound is disposed on the organic semiconductor layer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and/or other aspects will become apparent and more readily appreciated from the following description of the embodiments, taken in conjunction with the accompanying drawings in which.

DETAILED DESCRIPTION

Figure 1:
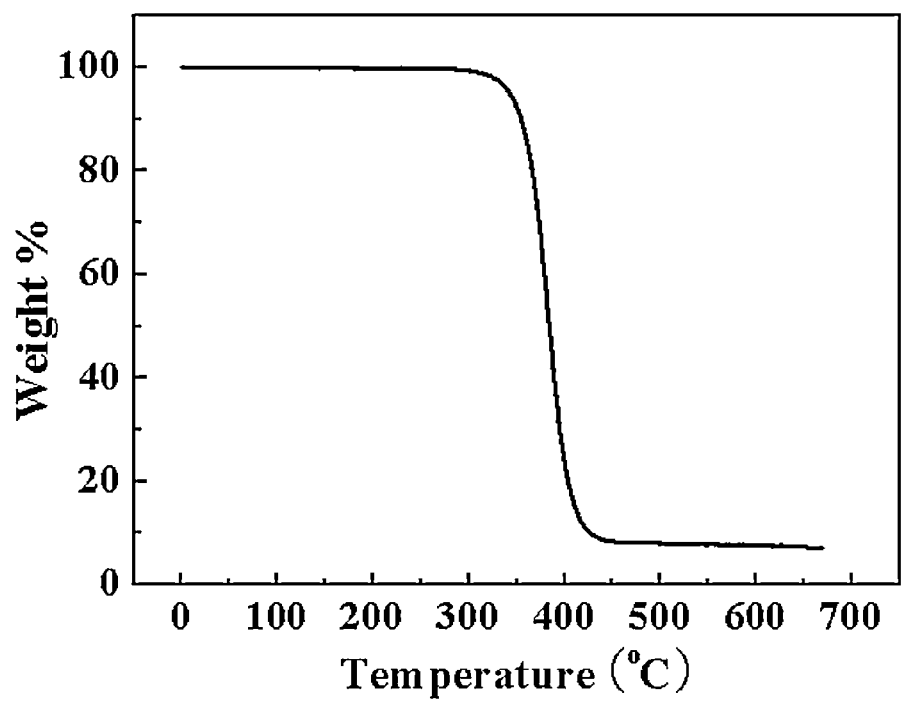
FIG. 1 is a graph of weight percent ("%") versus temperature (degrees centigrade, "° C.") illustrating thermogravimetric analysis ("TGA") results for dodecane substituted 2,6-bis (2-thienylvinyl)anthracene ("DOTVAnt")

Reference will now be made in detail to embodiments, examples of which are illustrated in the accompanying drawings. In this regard, the present embodiments may have different forms and should not be construed as being limited to the descriptions set forth herein. Accordingly, the embodiments are merely described below, by referring to the figures, to explain aspects of the present description. Like reference numerals refer to like elements throughout the specification.

It will be understood that when an element or layer is referred to as being on or "connected to" another element or layer, the element or layer can be directly on or connected to another element or layer or intervening elements or layers. In contrast, when an element is referred to as being "directly on" or "directly connected to" another element or layer, there are no intervening elements or layers present. As used herein, the term "and/or" includes any and all combinations of one or more of the associated listed items.

It will be understood that, although the terms first, second, third, etc., can be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the exemplary embodiments of the invention.

Spatially relative terms, such as "below," "lower," "upper" and the like, can be used herein for ease of description to describe one element or features relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "lower" relative to other elements or features would then be oriented "above" relative to the other elements or features. Thus, the exemplary term "below" can encompass both an orientation of above and below. The device can be otherwise oriented (rotated 90 degrees or at other orientations) and the spatially relative descriptors used herein interpreted accordingly.

As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

For example, an implanted region illustrated as a rectangle will, typically, have rounded or curved features and/or a gradient of implant concentration at its edges rather than a binary change from implanted to non-implanted region. Likewise, a buried region formed by implantation can result in some implantation in the region between the buried region and the surface through which the implantation takes place. Thus, the regions illustrated in the figures are schematic in nature and their shapes are not intended to illustrate the actual shape of a region of a device and are not intended to limit the scope of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Development of a low molecular-mass organic gelator ("LMOG") for use in organic solvents has been of enormous interest because it may construct 1D self-assembled nano- and microstructures via specific interactions, for example self-assembly. A 1D structure of LMOG based on π-conjugated molecules may be a powerful tool for providing effective charge-transport layers in devices such as organic transistors.

However, despite the potential possibilities for organic transistors, to the best of our knowledge, there is no documentation about the application of organic transistors based on organogel. Disclosed herein is a charge-transport layer in an organic electronic device using a 1D structure of well-ordered gelator based on π-conjugated molecules through gelation processes. Also disclosed is a method of manufacturing organic electronic devices by applying organogel processes to organic electronic devices. The organic semiconductor transistors may have excellent electrical characteristics.

Organic semiconductor transistors fabricated using gelation processes based on self-assembly of an organogel may have excellent electrical characteristics.

1D alignment of a rigid π-conjugated vinylene-based anthracene through a gelation processes is disclosed. Also disclosed is the first example of a nanofiber, derived from an organogel, successfully incorporated as an individual charge transport layer with a high electric field-effect mobility, about 0.48 cm$^2$/V·s, and an on/off ratio of about $10^5$ in a single nanofiber transistor. These results suggest that our strategy to form 1D organic structures based on a π-conjugated gelator in the organogel can provide high-performance single nanofiber organic transistors for use in low-cost, flexible electronic applications.

Additional aspects, advantages and features are set forth in the description which follows.

According to one or more embodiments, an organic nanofiber including a gelated organic semiconductor compound is disclosed. The organic nanofiber may be formed by gelating the organic semiconductor compound, which may self-assemble, in an organic solvent. The organic semiconductor compound may have a π-conjugated vinylene structure for improved gelation capability, and long alkyl chains to further improve gelation capability. The organic solvent may be a polar organic solvent to further improve gelation.

The organic nanofiber may be prepared by a gelation process that comprises an organic semiconductor compound represented by Formula 13 below:

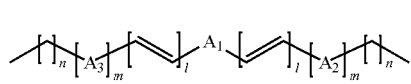

Formula 13 wherein $A_1$ is a $C_{10}$-$C_{20}$ arylene group or a $C_{10}$-$C_{20}$ heteroarylene group, $A_2$ and $A_3$ are each independently a $C_6$-$C_{20}$ arylene group or $C_2$-$C_{20}$ heteroarylene group, l is 0 or 1, m is in a range of about 1 to about 10, specifically in a range of about 1 to about 5, more specifically about 3, and n is in a range of about 1 to about 20, specifically in a range of about 9 to about 15, more specifically about 12. An arylene group is a bivalent aromatic ring system capable of having at least two rings, wherein the at least two rings may be connected or fused to each other. A heteroarylene group is a bivalent group in which at least one carbon atom of the arylene group is substituted with at least one atom selected from the group consisting of N, O, S and P.

In a particular embodiment, $A_1$ may be an anthracenylene group, a benzothieno benzothiophenylene group, a thiophenylene group, a naphthylene group, a phenylene group or a combination comprising at least one of the foregoing. $A_2$ and $A_3$ may be each independently a phenylene group, a naphthylene group, an anthracenylene group, a thiophenylene group, a benzothieno benzothiophenylene group or a combination comprising at least one of the foregoing.

In particular, the organic nanofiber may be prepared by a gelation process using the organic semiconductor represented by one selected from a group consisting of Formulae 1 to 12 below.

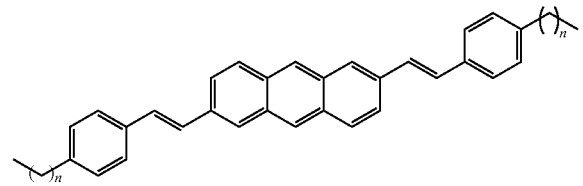

Formula 1 wherein n is in a range of about 1 to about 20, specifically in a range of about 9 to about 15, more specifically about 12,

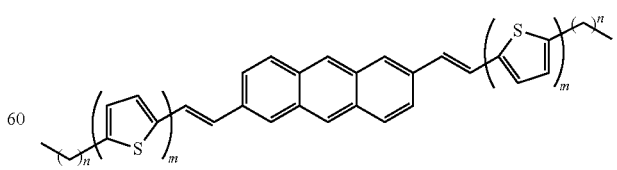

Formula 2 wherein n is in a range of about 1 to about 20, specifically in a range of about 9 to about 15, more specifically about 12, Formula 3 wherein m is in a range of about 1 to about 10, specifically in a range of about 1 to about 5, more specifically about 3, and n is in a range of about 1 to about 20, specifically in a range of about 9 to about 15, more specifically about 12, Formula 4

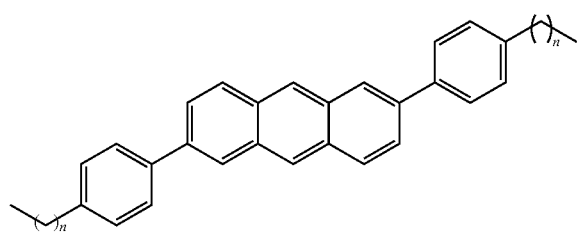

wherein n is in a range of about 1 to about 20, specifically in a range of about 9 to about 15, more specifically about 12, Formula 5

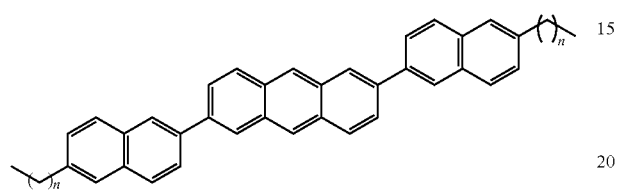

wherein n is in a range of about 1 to about 20, specifically in a range of about 9 to about 15, more specifically about 12, Formula 6

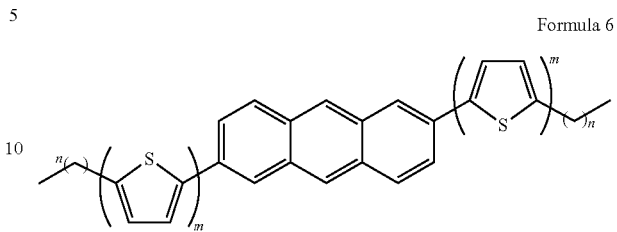

wherein m is in a range of about 1 to about 10, specifically in a range of about 1 to about 5, more specifically about 3, and n is in a range of about 1 to about 20, specifically in a range of about 9 to about 15, more specifically about 12, Formula 7

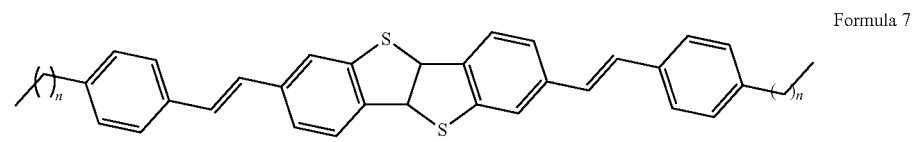

wherein n is in a range of about 1 to about 20, specifically in a range of about 9 to about 15, more specifically about 12, Formula 8

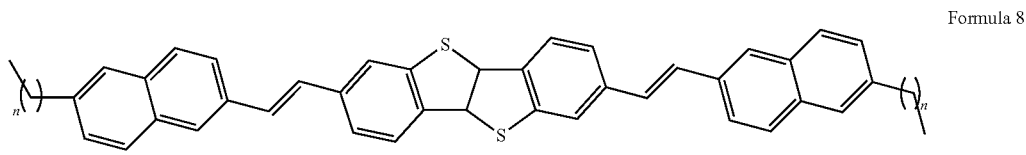

wherein n is in a range of about 1 to about 20, specifically in a range of about 9 to about 15, more specifically about 12, Formula 9

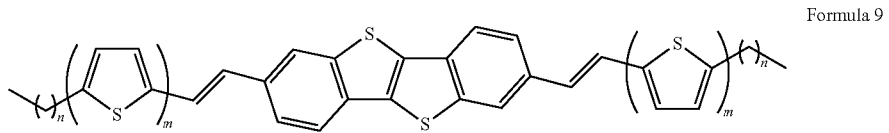

wherein m is in a range of about 1 to about 10, specifically in a range of about 1 to about 5, more specifically about 3, and n is in a range of about 1 to about 20, specifically in a range of about 9 to about 15, more specifically about 12, Formula 10

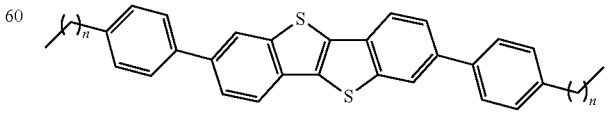

wherein n is in a range of about 1 to about 20, specifically in a range of about 9 to about 15, more specifically about 12, Formula 11

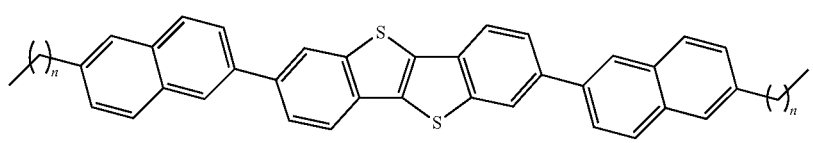

wherein n is in a range of about 1 to about 20, specifically in a range of about 9 to about 15, more specifically about 12 and Formula 12

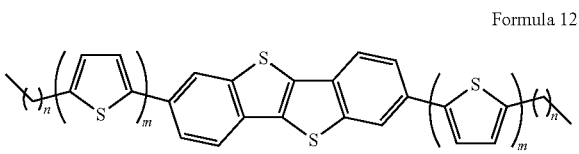

wherein m is in a range of about 1 to about 10, specifically in a range of about 1 to about 5, more specifically about 3, and n is in a range of about 1 to about 20, specifically in a range of about 9 to about 15, more specifically about 12 or a combination comprising at least one of the foregoing.

The organic solvent for gelating the compounds may be a polar organic solvent such as dimethyl sulfoxide ("DMSO"), or the like.

In one or more embodiments, disclosed is a method of manufacturing an organic semiconductor transistor. The method includes forming an organic nanofiber by gelating an organic semiconductor compound to form a self-assembled structure in an organic solvent; and forming a channel layer, which electrically connects a source electrode and a drain electrode, by disposing an organogel organic nanofiber in an organogel on a substrate, on which a source electrode and a drain electrode are disposed, wherein the source electrode and the drain electrode are insulated each other. For convenience, the organic semiconductor transistor may be fabricated in bottom contact geometry, wherein the channel layer is formed on the source and drain electrodes. The organic nanofiber may be prepared by adding an organic compound represented by a formula selected from the group consisting of Formulae 1 to 12 to an organic solvent. The organic solvent may be a polar organic solvent, for example DMSO.

According to one or more embodiments, an organic semiconductor transistor includes a substrate; a gate electrode; a source electrode and a drain electrode, which are insulated from the gate electrode; an organic semiconductor layer, which is insulated from the gate electrode and electrically connected to the source and drain electrodes; an insulating layer, which insulates the gate electrode from the source and drain electrodes and the organic semiconductor layer, wherein an organic nanofiber comprising a gelated organic semiconductor compound is disposed on the organic semiconductor layer. The organic semiconductor layer coated with the organic nanofiber may be formed in bottom contact geometry, wherein the channel layer is formed on the source and drain electrodes, or in top contact geometry, wherein the source and drain electrodes are formed on the channel layer. The organic nanofiber may be used, and the organic solvent may be DMSO for gelation.

One-dimensional (1D) alignment of a gelator, by formation of an organogel, may be driven by specific interactions, such as hydrogen bonding, van der Waals interactions, π-π stacking, and electrostatic interactions. Rigid thienylvinylene anthracene may be selected as a backbone because it can form strong π-π stacks and provide 1D aggregation. An embodiment is described with reference to the synthesis of 2,6-bis(2-thienylvinyl)anthracene ("TVAnt") substituted with dodecane ("DOTVAnt").

TVAnt substituted with alkyl groups is synthesized according to the scheme below.

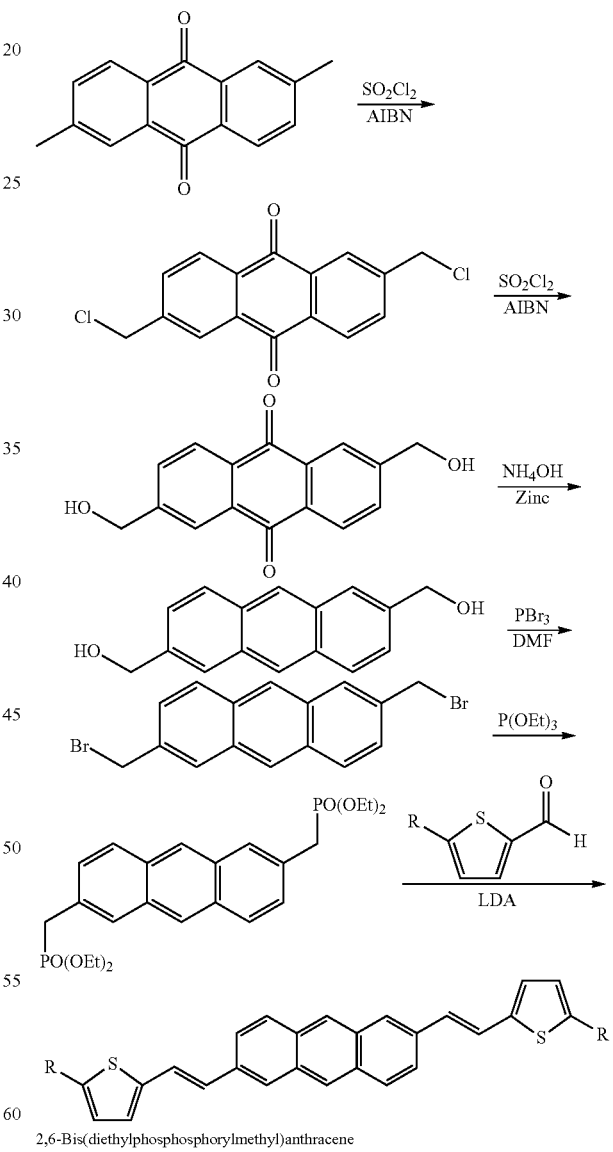

2,6-Bis(diethylphosphorylmethyl)anthracene

In the scheme, R of the last organic semiconductor compound is an alkyl group. In an embodiment, each R may independently have between about 1 and about 50 carbon atoms, specifically between about 2 and about 40 carbon atoms, more specifically about 20 carbon atoms. If R is a dodecyl group, the compound is DOTVAnt. Long alkyl chains may improve gelation capability. A vinyl group is formed by the reaction between a phosphonate group and an aldehyde group in the last reaction of the scheme. Strong π-π stacking interactions between an anthracene backbone and vinyl groups may improve gelation capability. Thus, various organic semiconductor compounds having excellent gelation capability may be prepared by introducing an aldehyde derivative. The alkyl chain of each R group may independently be a $C_{10}$ to $C_{16}$ group when n is in a range of about 1 to about 20, specifically in a range of about 9 to about 15, more specifically about 12, although gelation capability may vary according to the number of carbon atoms. However, the substituent is not limited thereto.

Figure 2:
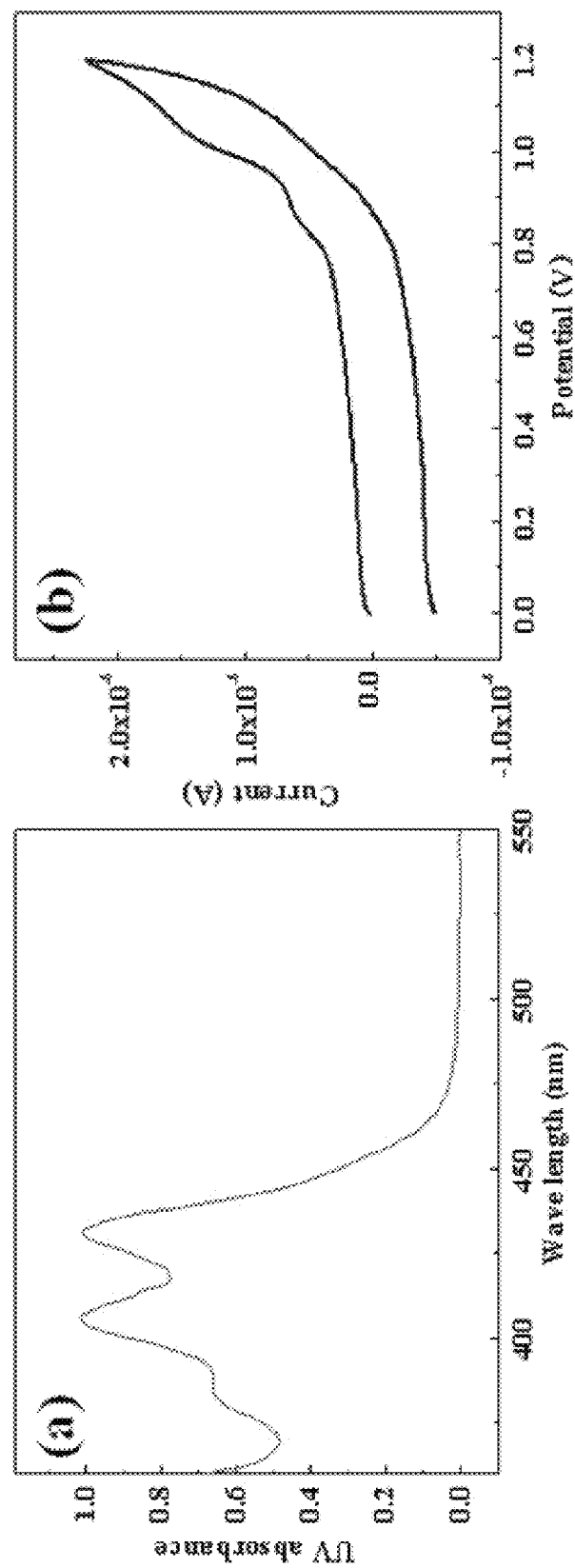
FIG. 2 is a graph illustrating (a) Ultraviolet-visible ("UV-VIS") absorption spectra of DOTVAnt in a graph of UV absorbance versus wavelength (nanometers, "nm"), and (b) a cyclic voltammogram ("CV") of DOTVAnt in a graph of current (amperes, "A") versus potential (volts, "V")

FIG. 1 is a graph illustrating thermogravimetric analysis ("TGA") results of DOTVAnt. The TGA analysis was performed using a TGA Q50 TA instrument at 10 degrees centigrade per minute ("° C.·min$^{-1}$") under a nitrogen atmosphere. Referring to FIG. 1, DOTVAnt has thermal stability greater than that of pentacene, which is thermally decomposed at 260 ° C. FIG. 2A is a graph illustrating UV-vis absorption spectra of DOTVAnt. FIG. 2B is a graph illustrating a cyclic voltammogram of DOTVAnt. Referring to FIG. 2, DOTVAnt has greater oxidative stability than pentacene.

Figure 3:
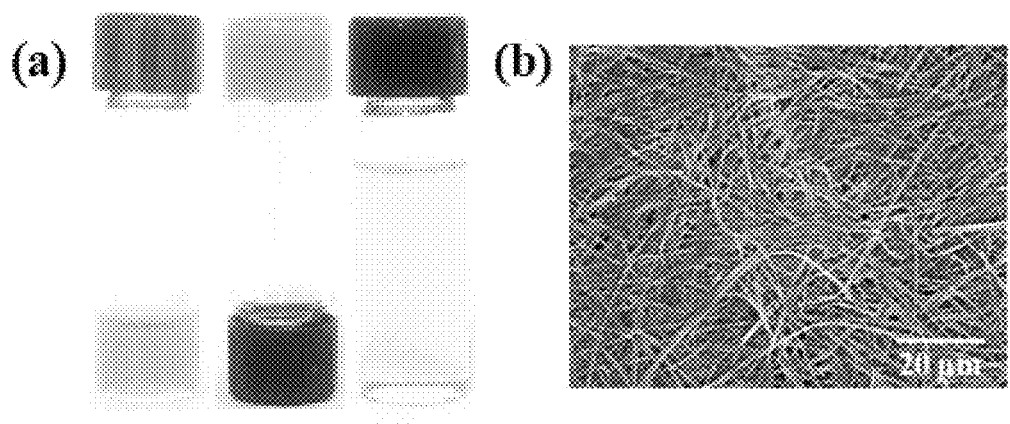
FIG. 3 is (a) a photographic image of DOTVAnt (1.0 weight/volume percent, "wt/vol %") dissolved in dimethyl sulfoxide ("DMSO") (left vial), the corresponding organogel at room temperature (middle vial), and a dilute dispersion of DOTVAnt xerogel in chloroform, and (b) a scanning electron microscopic ("SEM") image of dried DOTVAnt xerogel.

The gelation capability of the DOTVAnt may be measured by dissolving the DOTVAnt in various solvents. DOTVAnt (10 milligrams, "mg") is added to DMSO (1 milliliter, "mL"), and the mixture is refluxed until the DOTVAnt is dissolved to prepare an organogel. FIG. 3 is a photographic image of DOTVAnt (1.0 weight/volume percent, "wt/vol %", determined as grams DOTVnt per 100 mL of solution) dissolved in DMSO (left vial), the corresponding organogel at room temperature (middle vial), and dilute dispersion of DOTVAnt xerogel in chloroform (right vial). Image (b) of FIG. 3 is a scanning electron microscopic ("SEM") image of dried DOTVAnt xerogel. Images (a) and (b) of FIG. 3 show well-dispersed characteristics of DOTVAnt in chloroform. In order to observe the morphology of DOTVAnt gelator in the organogel, the dried gel (xerogel) was analyzed using SEM. Referring to (b) of FIG. 3, three dimensional fibrous network structures of DOTVAnt gelator are formed using a gelation process. Such gelation capability of DOTVAnt shows that the driving force is derived from a strong π-π stacking interaction of thienylvinylene anthracene backbones and van der Waals interactions between the long alkyl chains.

Figure 4:
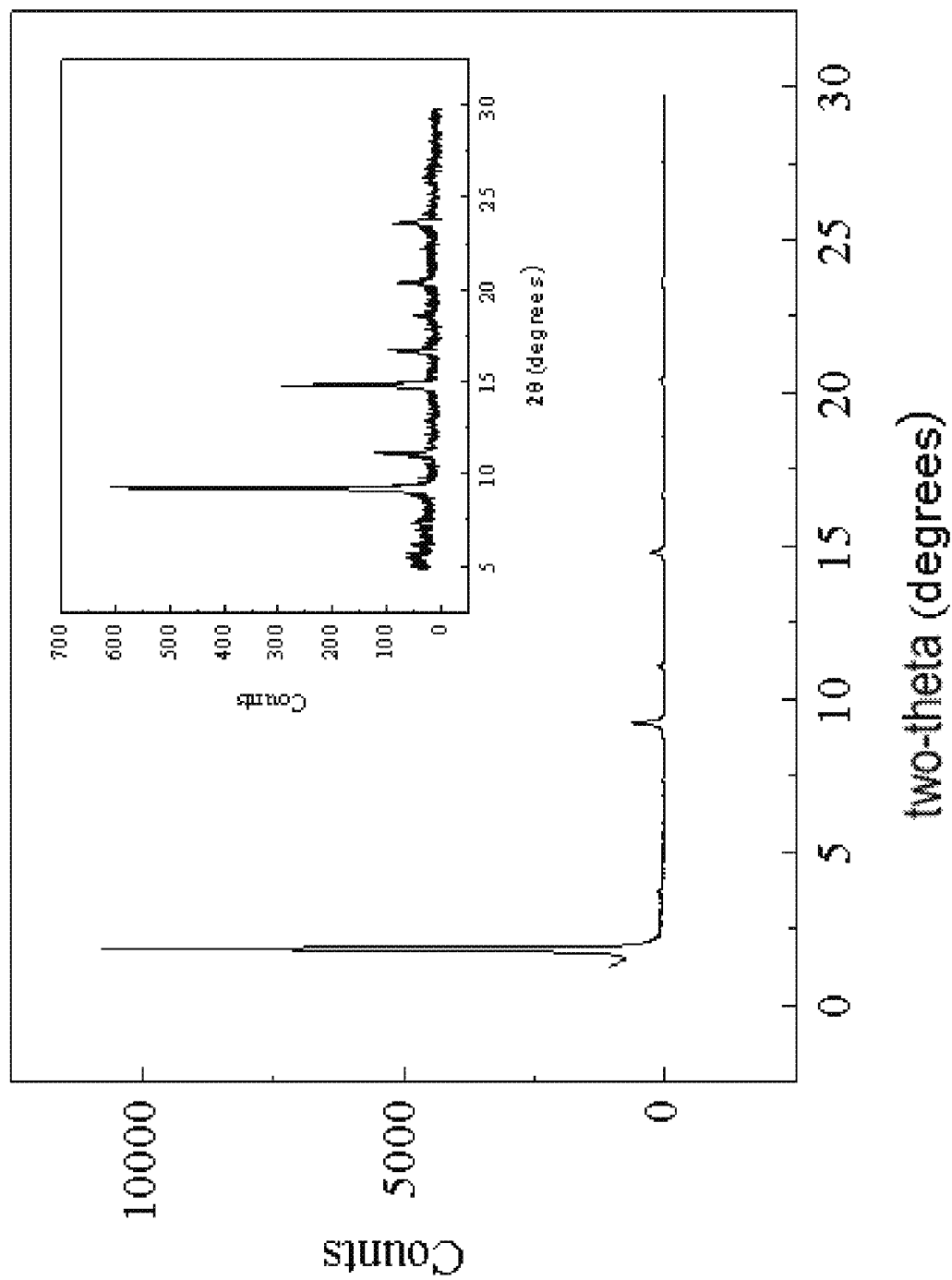
FIG. 4 is a graph illustrating an X-ray diffraction ("XRD") pattern of DOTVAnt xerogel in a graph of counts versus degrees two-theta ("$2\theta$"), and the inset graph shows an enlarged part of the pattern ranging from 5° to 30° $2\theta$.
Figure 5:
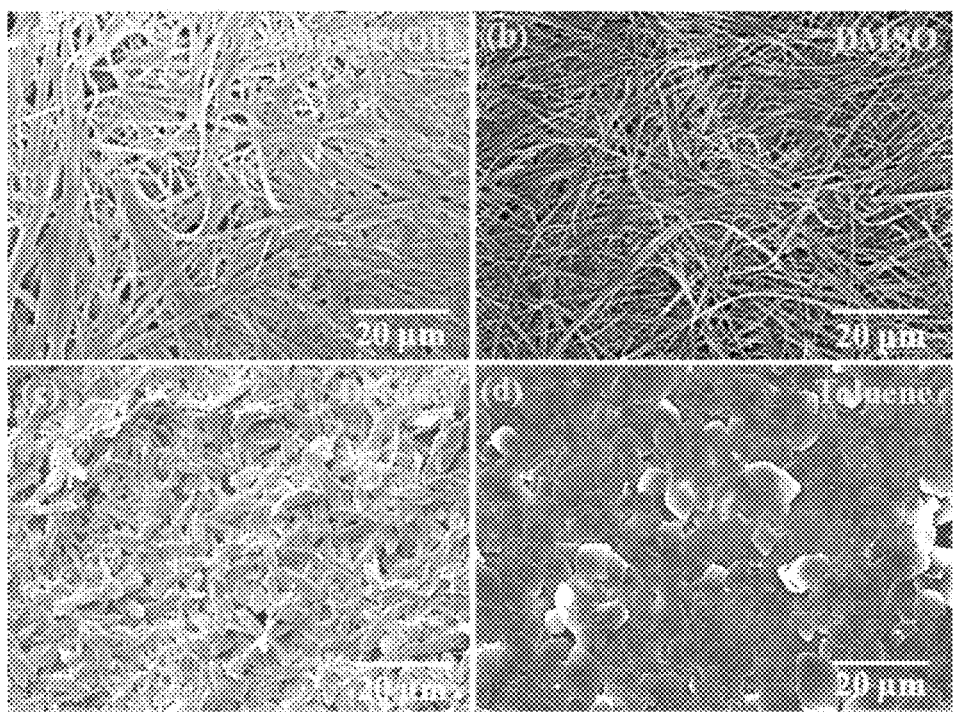
FIG. 5 illustrates SEM images of DOTVAnt from the solvents (a) 2-ethoxy ethanol, (b) DMSO, (c) decane, and (d) toluene.

FIG. 4 is a graph illustrating an X-ray diffraction ("XRD") pattern of DOTVAnt xerogel. The inset graph shows the enlarged part of the pattern ranging from 5° to 30° two-theta. Sharp XRD peaks indicate that DOTAnt xerogel has a highly ordered crystalline structure. Inherent dimensions of DOTVAnt fibers are determined by SEM and atomic force microscopy ("AFM"). In addition, belt-like microstructures of DOTVAnt gelator are obtained in the organogel by using 2-ethoxyethanol as a solvent. 1D micro/nanostructures of DOTVAnt gelators in organogel may be formed using a polar organic solvent, such as DMSO, 2-ethoxyethanol, or the like or a combination comprising at least one of the foregoing. The morphology of some different microstructures is obtained using a nonpolar solvent without organogel formation. Images (a) to (d) of FIG. 5 illustrate SEM images of DOTVAnt in different solvents. Nanofibers (or nanowires) are observed when using DMSO, and belt-like structures are observed when using 2-ethoxyethanol. Nano- and microstructures may be formed in polar solvents by gelation.

Figure 6:
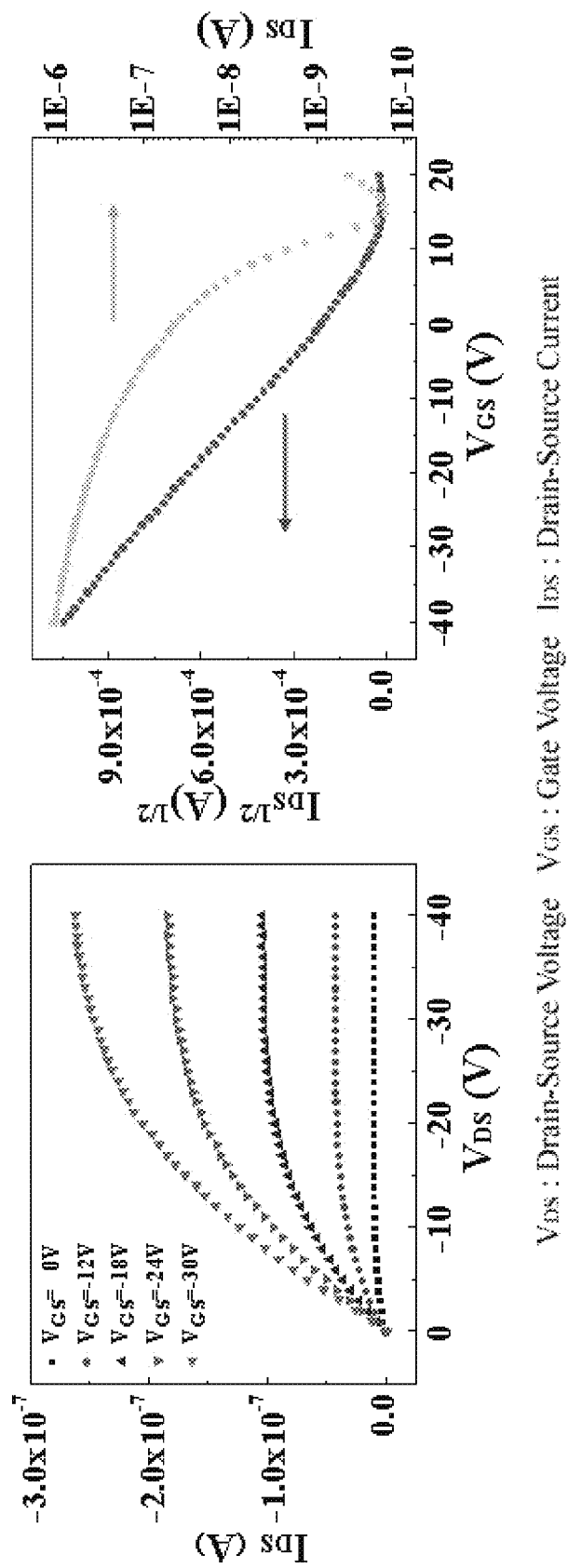
FIG. 6 is a series of graphs illustrating electrical characteristics of organic thin film transistors ("OTFTs") based on DOTVAnt films via existing solution processes, including a graph of source-drain current versus source-drain voltage and a graph of the square root of the source-drain current and the source-drain current versus gate voltage.

Before measuring electrical properties of a 1D structure of the DOTVAnt nanofibers according to an embodiment, the DOTVAnt film is used as an active channel layer. Since DOTVAnt molecules are not soluble or have limited solubility in any other solvents, they may be dissolved in toluene by heating the solvent. Electrical characteristics of organic thin film transistors ("OTFTs") based on DOTVAnt films exhibit p-type characteristics with an estimated hole mobility in a range of about 0.02 to about 0.05 square centimeters per volt seconds ("cm$^2$/V·s") in the saturation region. FIG. 6 is a series of graphs illustrating electrical characteristics of OTFTs based on DOTVAnt films via existing solution processes.

Figure 7:
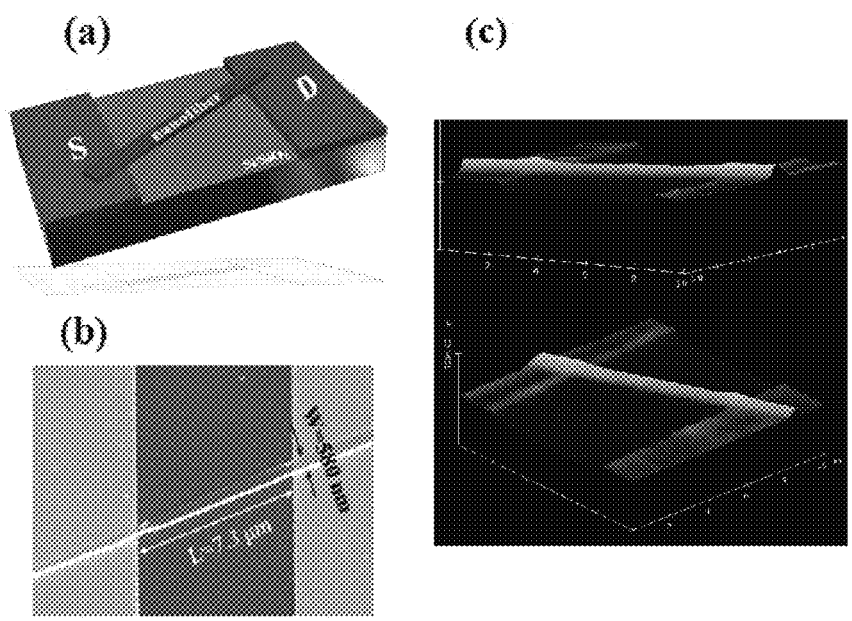
FIG. 7 is (a) a schematic view of a DOTVAnt transistor including an individual nanofiber, (b) an SEM image of a bottom-contact single nanofiber transistor including DOTVAnt, and (c) an atomic force microscope ("AFM") image of the corresponding transistor.
Figure 8:
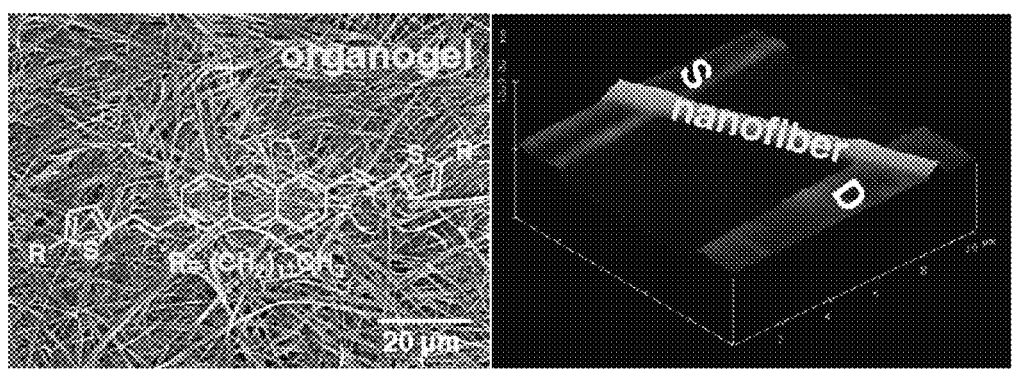
FIG. 8 illustrates a SEM image of DOTVAnt organogel (left) and an AFM image of source and drain electrodes and a nanofiber channel layer (right)

In order to measure electrical characteristics of the DOTVAnt according to an embodiment, a bottom-contact DOTVAnt transistor based on individual nanofibers is prepared. DOTVAnt gel (xerogels) dispersed in chloroform is spin-coated on Cr/Au (2 nanometer, "nm"/40 nm thickness, respectively) electrodes, which are pre-patterned on a hexamethyldisilazane ("HMDS")-treated SiO$_2$/Si substrate. FIG. 7A is a schematic view of a DOTVAnt transistor from an individual nanofiber. FIG. 7B is a SEM image of a bottom-contact single nanofiber transistor of DOTVAnt. FIG. 7C is an AFM image of the corresponding transistor. FIG. 8 illustrates a SEM image of DOTVAnt in organogel and an AFM image of source and drain electrodes and a nanofiber channel layer.

Figure 9:
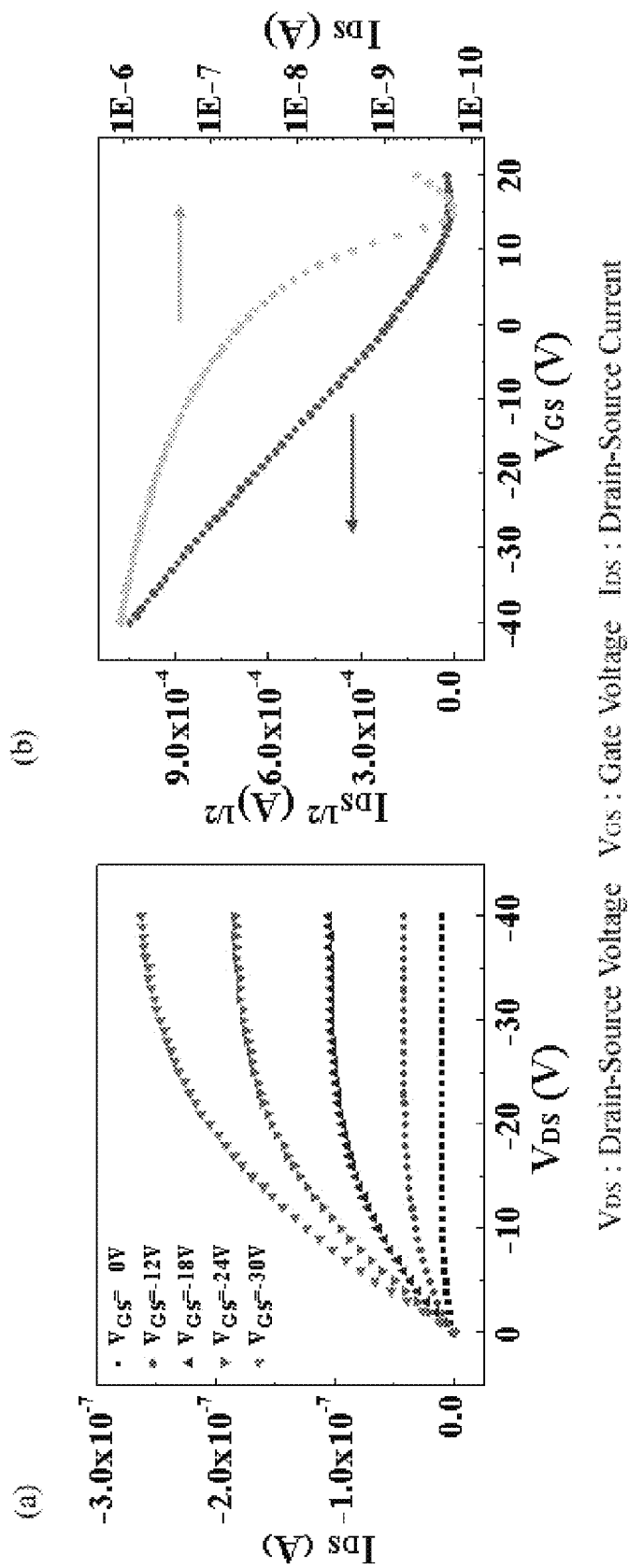
FIG. 9 is (a) a graph illustrating output characteristics of a single DOTVAnt nanofiber transistor in a graph of source-drain current versus source-drain voltage, and (b) a graph illustrating transfer characteristics of a single DOTVAnt nanofiber transistor in a graph of the square root of source-drain current and source-drain current versus gate voltage.

Graph (a) of FIG. 9 is a graph illustrating output characteristics of a single DOTVAnt nanofiber transistor, and graph (b) of FIG. 9 is a graph illustrating transfer characteristics of a single DOTVAnt nanofiber transistor. Field-effect mobility ("μ") is extracted from the slope in the saturation regime (Source-Drain Voltage "$V_{DS}$"=−30V) and a width to length ratio ("W/L") is defined as a ratio of the width of the nanofiber to a distance between the source electrode and the drain electrode. The single nanofiber transistor exhibits p-type characteristics with an estimated μ of holes of about 0.48 cm$^2$/v·s in the saturation region and an on/off ratio of $10^5$. Referring to the result, the transistor performance of DOTVAnt based on the single nanofiber is much better that of an existing solution processed transistor based on thin films. This result may explain that 1D alignment of well-ordered DOTVAnt molecules through gelation process and a lack of grain boundaries provides an effective charge transport layer comparable to that of a thin film layer.

Figure 10:
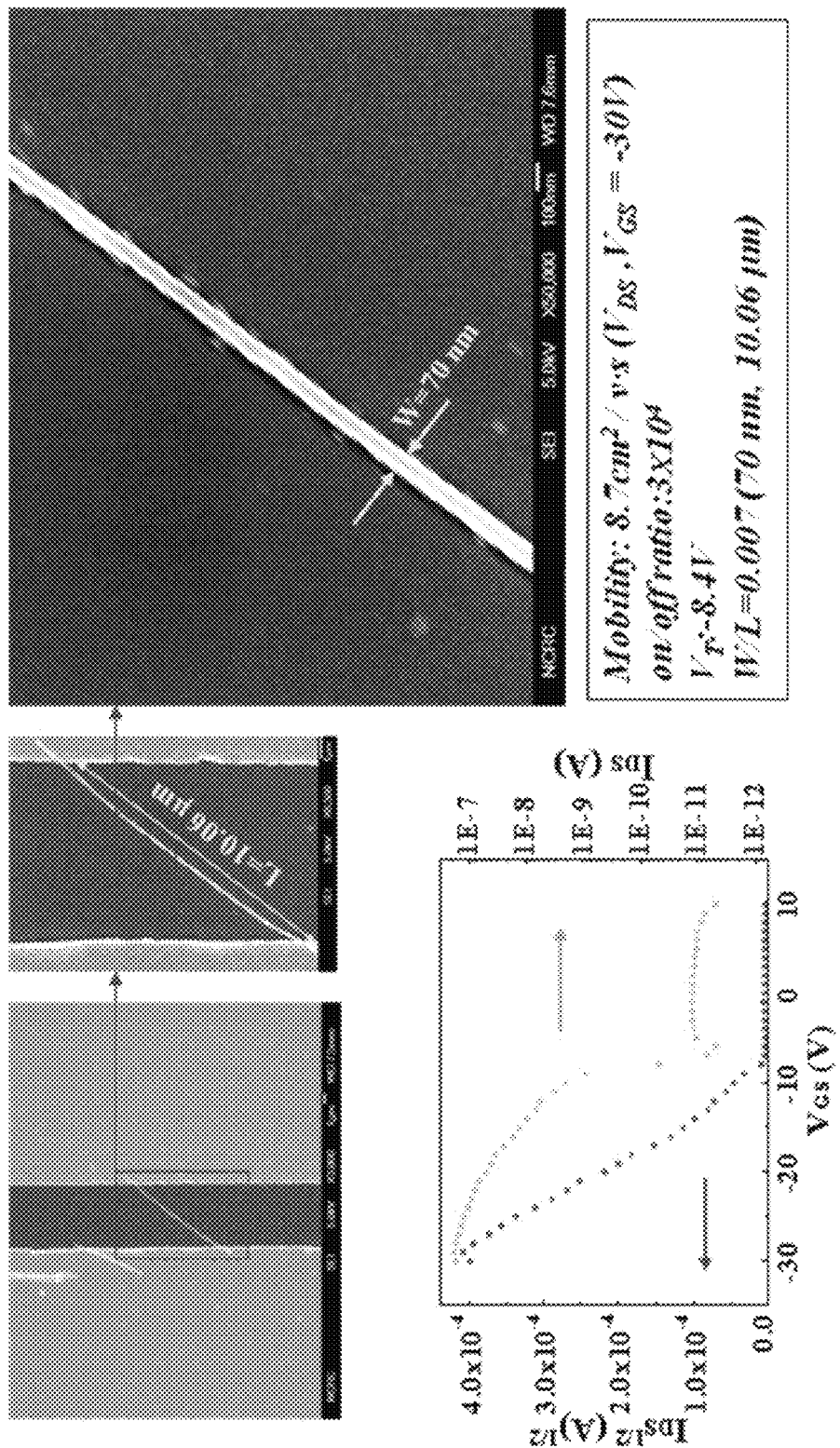
FIG. 10 illustrates a high mobility (up to 8.7 square centimeters per volt seconds, "$cm^2/Vs$") obtained from a nanofiber with a width of 70 nanometers ("nm"), including a graph of the square root of source-drain current and source-drain current versus gate voltage.

FIG. 10 illustrates a high mobility (up to 8.7 cm$^2$/V·s) obtained from a nanofiber with a width of 70 nm.

However, current-voltage ("I-V") characteristics may not be obtained in the case of the single nanofiber transistor due to insufficient contact at an interface between a metal and a semiconductor.

1D arrangement of rigid π-conjugated vinylene-based anthracene through the gelation process is described herein. In addition, a nanofiber based on organogel is introduced, and an individual charge transport layer with high field-effect mobility and on/off ratio in a single nanofiber transistor is successfully incorporated. These results show that 1D organic structures based on π-conjugated gelator in organogel may be used for a high performance single nanofiber organic transistor in a low-cost, flexible electronic application.

An embodiment is described in more detail with reference to the examples below. However, these examples are for illustrative purposes only and are not intended to limit the scope of the invention.

$^1$H and $^{13}$C NMR spectra were recorded in CDCl$_3$ using an Advance 300 MHz Bruker spectrometer. The $^1$H NMR chemical shifts in CDCl$_3$ corresponding to CHCl$_3$ (7.27 ppm) and $^{13}$C NMR chemical shifts in CDCl$_3$ corresponding to CHCl$_3$ (77.23 ppm) were measured.

Physical Measurement

TGA analyses were performed using a TGA Q50 TA instrument at 10° C.·min$^{-1}$ under a nitrogen atmosphere.

Absorption spectra of a DOTVAnt dissolved in toluene were recorded on an Agilent 8453 spectrometer. Cyclic voltammograms of the DOTVAnt dissolved in dichlorobenzene with tetrabutylammonium hexafluorophosphate (Bu$_4$NPF$_6$, 0.1 molar, "M") as a supporting electrolyte were measured on a CHI 700C electrochemical instrument at a scan rate of 100 millivolts per second ("mV/s"). Counter and working electrodes were formed of Pt and a reference electrode was formed of Ag/AgCl. All potentials were calibrated with a standard ferrocene/ferrocenium (Fc/Fc$^+$) redox couple (E$^{1/2}$=+0.26 volts, "V"). A measured energy level of DOTVAnt was equal to or less than 5.31 electron volts ("eV").

XRD analyses were carried out with a Rigaku diffractometer at a wavelength of 1.5418 Å at 298 K.

Fabrication of Single Nanofiber Transistor and Measurement of Electrical Characteristics Single nanofiber transistors were fabricated using bottom contact geometry. A heavily doped silicon wafer was used as a gate electrode, a HMDS treated SiO$_2$ layer (thickness of equal to or less than 300 nanometers, "nm") was used as a gate dielectric layer. Cr/Au (2 nm and 40 nm, respectively) was thermally evaporated to form source and drain electrodes and patterned using photolithography and lift off methods. The resulting bottom contact substrates consisted of arrays having the dimensions 1000 micrometers ("µm") by 1000 µm and square electrodes with a 5 to 10 µm channel gap. Then, well-dispersed nanofibers of DOTVAnt in chloroform (0.01 milligrams per milliliter, "mg/mL") were spin-coated at a rate of equal to or less than 3000 revolutions per minute ("rpm") onto the patterned electrode substrate. To find single fiber bridged the source and drain electrodes, the resulting coated substrate was observed using a light microscope. The electrical characterization of a single nanofiber transistor was performed at room temperature in air using a Keithley 4200-SCS semiconductor. The W/L ratio of the nanofibers was observed using a field-emission scanning electron microscopic device (FE-SEM, JSM7401F, JEOL). In addition, it was reconfirmed that there was only one nanofiber bridged between the source and the drain in the single nanofiber transistors. Field-effect mobility ("µ") was obtained in the saturation regime (source-drain voltage ("V$_{DS}$")=−30 V) in the plot of the square-root of drain current versus the gate voltage "V$_{GS}$" using the following equation.

$$I_{DS} = \frac{WC_i}{2L}\mu(V_{GS} - V_T)^2$$

Here, I$_{DS}$ is the source-drain saturation current; C$_i$ (1.1× 10$^{-8}$ farads ("F") is the capacitance of the SiO$_2$ insulator, W/L is a ratio of the width of the nanofiber to the length across the source and drain electrodes, and V$_{GS}$ and V$_T$ are the gate and the threshold voltages, respectively.

Synthesis of Organic Semiconductor Compound

All chemicals were purchased from Aldrich and Lancaster. The synthesis of DOTVAnt will be described. Other organic semiconductor compounds having anthracene backbones may be prepared by modifying substituents based on the method described above.

Synthesis of DOTVAnt 2,6-Bis(cholormethyl)anthraquinone 2,6-Dimethylanthraquinone (3.8 grams, "g", 16.09 millimoles, "mmol"), SO2Cl$_2$ (50 mL), and 2,2'-azobis(2-methyl propionitrile) (0.16 g, 0.96 mmol) were mixed, and the mixture was refluxed for 24 hours. An excess amount of SO$_2$Cl$_2$ was removed by distillation in a vacuum. A solid residue was filtered, washed with petroleum ether several times and recrystallized from DMF to obtain 3.8 g (78%) of 2,6-bis (cholormethyl)anthraquinone.

$^1$H NMR (300 MHz, CDCl$_3$): δ8.41 (m, 4H), 7.98 (s, 2H), 5.00 (s, 4H). High-resolution mass spectrometry ("HRMS"): Calculated for C$_{16}$H$_{10}$C$_{12}$O$_2$ 304.0057. Found: 304.0034.

2,6-Bis(hydroxymethyl)anthraquinone

A suspension of 2,6-bis(cholormethyl)anthraquinone (3.5 g, 11.47 mmol) was refluxed in 300 mL of water and 400 mL of DMSO while vigorously stirring. The mixture was heated for 4 hours to obtain a clear solution. The resulting solution was refluxed for 38 hours and cooled to room temperature. Crystalline products were collected by filtration and recrystallized from DMF to obtain 3.0 g (98%) of 2,6-bis(hydroxymethyl)anthraquinone.

$^1$H NMR (300 MHz, DMSO-d6): δ8.17 (m, 4H), 7.85 (d, 2H, J=10.7 Hz), 5.57 (s, 2H), 4.70 (s, 4H). HRMS: Calculated for C$_{16}$H$_{12}$O$_4$ 268.0735. Found: 268.0749.

2,6-Bis(dihydroxymethyl)anthracene

Zinc powder (6.0 g) was added to a solution of 2,6-bis (hydroxymethyl)anthraquinone (2.8 g 10.43 mmol) in ammonium hydroxide (70 mL). The mixture was refluxed overnight. Then, undissolved materials were removed by filtration and washed with DMSO. The solution was precipitated in 200 mL of 1N HCl. Products collected by filtering the solution were 2,6-bis(dihydroxymethyl)anthracene (1.86 g, 75%).

$^1$H NMR (300 MHz, DMSO-d6): δ8.49 (s, 2H), 8.04 (d, 2H, J=8.7 Hz), 7.94 (s, 2H), 7.46 (d, 2H, J=8.7 Hz), 5.40 (t, 2H, J=5.6 Hz), 4.69 (d, 4H, J=5.6 Hz). HRMS: Calculated for C$_{16}$H$_{14}$O$_2$ 238.0994. Found: 238.1003.

2,6-Bis(dibromomethyl)anthracene

PBr$_3$ (4.4 g, 16.30 mmol) was added dropwise to a suspension of 2,6-bis(dihydroxymethyl)anthracene (1.5 g, 6.29 mmol) in DMF (30 mL) at 0° C. Upon formation of yellow precipitation, the mixture was heated to room temperature and stirred for 4 hours. Solid products were collected by filtration and washed with water and hexane to obtain yellow solid 2,6-bis(dibromomethyl)anthracene (2.2 g, 98%). The products were recrystallized from DMF to obtain purified products.

$^1$H NMR (400 MHz, DMSO): δ8.56 (s, 2H), 8.15 (s, 2H), 8.12 (d, 2H, J=11.5 Hz), 4.93 (s, 4H). HRMS: Calculated for C$_{16}$H$_{12}$Br$_2$ 361.9306. Found: 361.9277.

2,6-Bis(diethylphosphorylmethyl)anthracene 2,6-Bis(dibromomethyl)anthracene (2.2 g, 6.04 mmol) was added to triethylphosphite (50 mL), and the resulting solution was refluxed for 12 hours. The solvent was removed in a vacuum, and the residue was purified by column chromatography on silica gel using ethyl acetate/dichloromethane (2:1) as an eluent. The yield was 90%.

$^1$H NMR (300 MHz, CDCl3): δ8.49 (s, 2H), 8.04 (d, 2H, J=8.7 Hz), 7.94 (s, 2H), 7.46 (d, 2H, J=8.7 Hz), 5.40 (t, 2H, J=5.6 Hz), 4.69 (d, 4H, J=5.6 Hz). $^{13}$C NMR (300 MHz, CDCl3): 131.54, 130.83, 128.75, 128.61, 128.39, 127.84, 125.67, (62.26, 62.16), (35.10, 33.27), (16.44, 16.30). MS (EI) m/z: (M+) calculated for $C_{24}H_{32}O_6P_2$ 478.16; found 478.

2,6-Bis[2-(5-dodecylthienyl)vinyl]anthracene (DOTVAnt)

Lithium diisopropylamide ("LDA") (1.5 M in cyclohexane, 3.2 mL, 5.75 mmol) was added dropwise to a solution of 2,6-bis(diethylphosphorylmethyl)anthracene (1.4 g, 2.92 mmol) in anhydrous tetrahydrofuran ("THF") (50 mL) at -78° C. under a nitrogen atmosphere while stirring. The mixture was stirred for 1 hour and then 5-dodecylthiophene-2-carbaldehyde (2.30 g, 8.20 mmol) in THF (20 mL) was added dropwise thereto over a period of 10 minutes. After the mixture was stirred for 2 hours at -78° C. and for 12 hours at room temperature, 5 mL of water was added thereto and the solvent was evaporated. The residue was washed with water and MeOH. The desired product was separated by washing.

HRMS: Calculated for $C_{50}H_{66}S_2$ 730.4606. Found: 730.4604. Analysis Calculated: C, 82.13; H, 9.10; S, 8.77; Found: C, 82.11; H, 9.06; S, 8.83.

Organic semiconductor compounds prepared by substituting TVAnt backbones with alkyl groups may be similarly synthesized. Organic semiconductor compounds prepared by substituting anthracene backbones with vinyl groups and compounds without vinyl groups may also be prepared. The anthracene-based organic semiconductor compound according to the present embodiment may be efficiently used for gelation.

In addition, a process of introducing a benzothieno benzothiophene ("BTBT") backbone into organic semiconductor compounds and a process of synthesizing the BTBT is described.

The BTBT backbone is synthesized according to the scheme below.

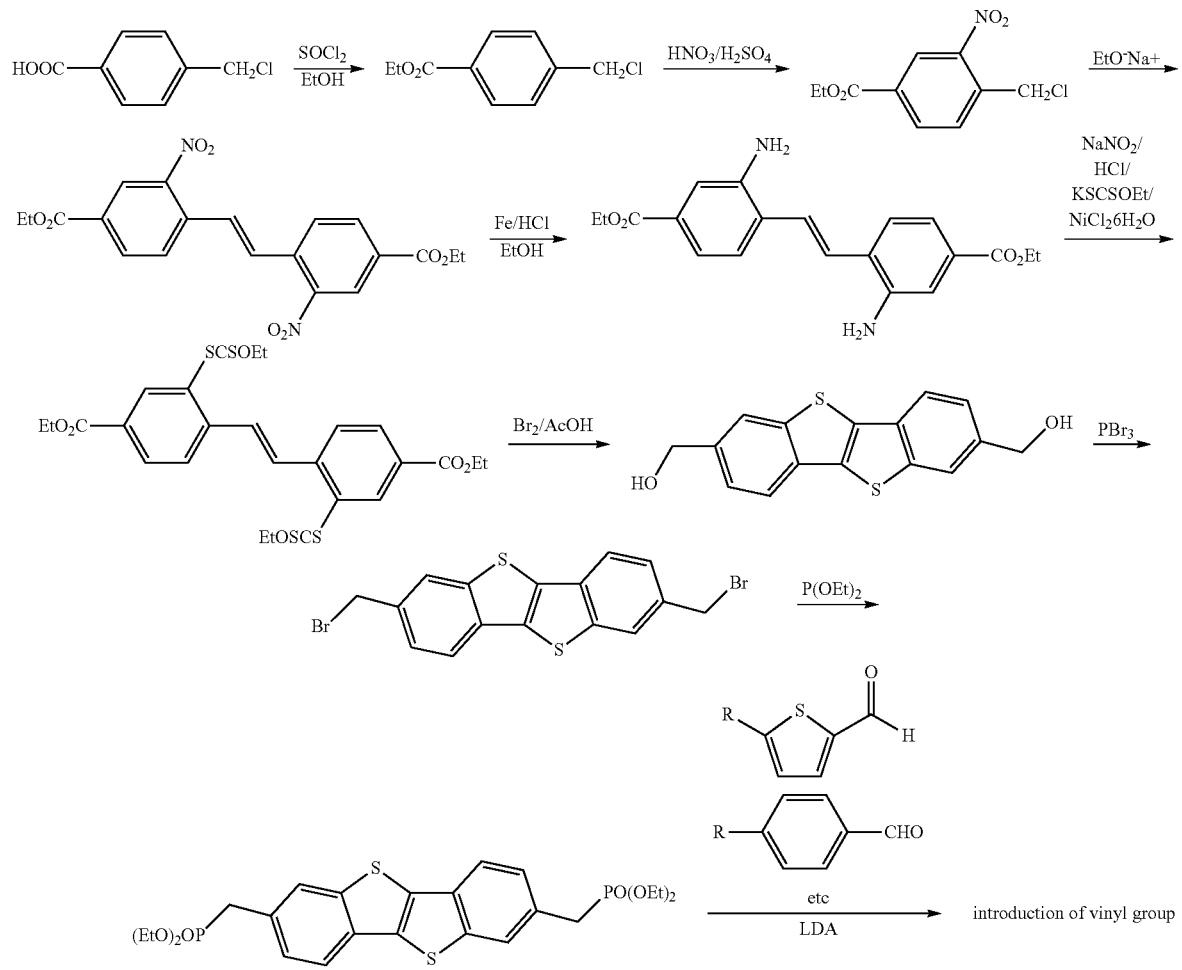

Synthesis of BTBT Backbone

2,7-Bis(dihydroxymethyl)[1]benzothieno[3,2-b]benzothiophene

LiAlH$_4$(0.74 g, 19.5 mmol) was added to [1]benzothieno[3,2-b]benzothiophene 2,7-dicarboxylate (1.50 g 3.9 mmol) in THF (40 mL). The mixture was stirred overnight. Insoluble materials were removed by filtration and washed with hot DMSO. The solution was precipitated in 50 mL of 1 normal ("N") HCl. The product was collected by filtration to obtain 1.86 g (75%) of pure 2,7-bis(dihydroxymethyl)[1]benzothieno[3,2-b]benzothiophene.

$^1$H NMR (300 MHz, DMSO) data is as follows:

δ8.05 (s, 2H), 7.98 (d, 2H, J=8.1 Hz), 7.48 (d, 2H, J=8.2 Hz), 5.38(t, 2H, J=5.6 Hz), 4.69 (d, 4H, J=5.3 Hz).

2,7-Bis(dibromomethyl)[1]benzothieno[3,2-b]benzothiophene

Phosphorus tribromide (3.24 g, 11.9 mmol) was added dropwise to a suspension of 2,7-bis(dihydroxymethyl)[1]benzothieno[3,2-b]benzothiophene (0.9 g, 2.99 mmol) in DMF (20 mL) at 0° C. Upon formation of yellow precipitation, the mixture was heated to room temperature and stirred for 4 hours. Solid products were collected by filtration and washed with water and hexane to obtain yellow solid 2,6-bis(dibromomethyl)anthracene (1.1 g, 78%). The product was further purified by recrystallization from DMF.

$^1$H NMR (300 MHz, DMSO) data is as follows:
δ8.24 (s, 2H), 8.08(d, 2H, J=8.2 Hz), 7.63 (d, 2H, J=8,1 Hz), 4.91 (s, 4H).

2,7-Bis(diethylphosphorylmethyl) [1]benzothieno[3,2-b] benzothiophene)

2,6-Bis(dibromomethyl)anthracene (1.1 g, 2.58 mmol) was added to triethylphosphite (30 mL), and the resulting solution was refluxed for 12 hours. The solvent was removed in a vacuum, and the residue was purified by column chromatography on silica gel using ethyl acetate/dichloromethane (2:1) as an elutent. Yield (90%).

$^1$H NMR (300 MHz, CDCl$_3$) data are as follows:
δ7.87(s, 2H), 7.84 (d, 2H, J=8.2 Hz), 7.42 (d, 2H, J=8.1 Hz), 4.05 (m, 8H), 3.36 (d, 4H, J=21.5 Hz), 1.27 (t, 12H, J=7.0 Hz). $^{13}$C NMR (75 MHz, CDCl$_3$): (142.62, 142.58), 133.18, 131.90, (128.79, 128.67), (126.92, 126.84), (124.98, 124.88), 121.40, (62.33, 62.24), (34.81, 32.97), (16.45, 16.37).

As shown in the scheme, a vinyl group may be introduced to the backbone through Horner-Emmons coupling between a phosphonate derivative and an aldehyde derivative by introducing various aldehyde derivatives thereto. In addition, an alkyl-substituted phenyl group, an alkyl-substituted thiophenyl group, an alkyl-substituted naphthyl group, or the like or a combination thereof may be introduced into the BTBT backbone according to the scheme. Thus, the resulting compounds have gelation capability.

As described above, according to the one or more of the above embodiments, nanofibers based on organogel are introduced into an organic semiconductor compound. When a thin film is formed using a solution process, well-ordered structures may not be obtained, and thus electrical characteristics may be decreased. However, according to one or more of the above embodiments, an efficient and high performance charge transport layer may be obtained. The organic thin film transistor according to one or more of the above embodiments has excellent performance, may be applied to a flexible electronic device and may be fabricated inexpensively.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. An organic semiconductor transistor comprising:
   a substrate;
   a gate electrode;
   a source electrode and a drain electrode, each of which are insulated from the gate electrode;
   an organic semiconductor layer, which is insulated from the gate electrode and electrically connected to the source and drain electrodes; and
   an insulating layer, which insulates the gate electrode from the source and drain electrodes and the organic semiconductor layer,
   wherein an organic nanofiber comprising a gelated organic semiconductor compound is disposed on the organic semiconductor layer, and
   wherein the gelated organic semiconductor compound comprises end groups of the formula

wherein n is in a range of about 9 to about 15 and * represents a point of attachment.

2. The organic semiconductor transistor of claim 1, formed by self-assembly of the gelated organic semiconductor compound in an organic solvent.

3. The organic semiconductor transistor of claim 1, wherein the organic semiconductor layer is formed using bottom contact geometry and the channel layer is formed on the source and drain electrodes, or wherein the organic semiconductor layer is formed using top contact geometry and the source and drain electrodes are formed on the channel layer.

4. The organic semiconductor transistor of claim 1, wherein the organic semiconductor compound is represented by Formula 13:

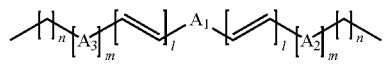

wherein A$_1$ is a C$_{10}$-C$_{20}$ arylene group or a C$_{10}$-C$_{20}$ heteroarylene group,
   A$_2$ and A$_3$ are each independently a C$_6$-C$_{20}$ arylene group or a C$_2$-C$_{20}$ heteroarylene group, and
   l is 0 or 1, m is 1 to about 5, and n is in a range of about 9 to about 15.

5. The organic semiconductor transistor of claim 1, wherein the organic nanofiber comprises a compound represented by a formula selected from the group consisting of Formulas 1 to 12:

Formula 1

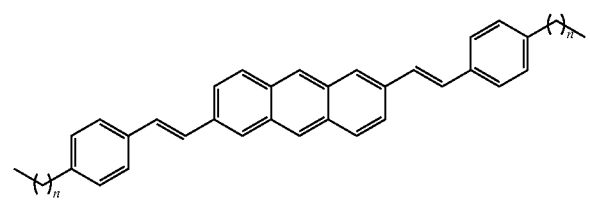

wherein n is in a range of about 9 to about 15,

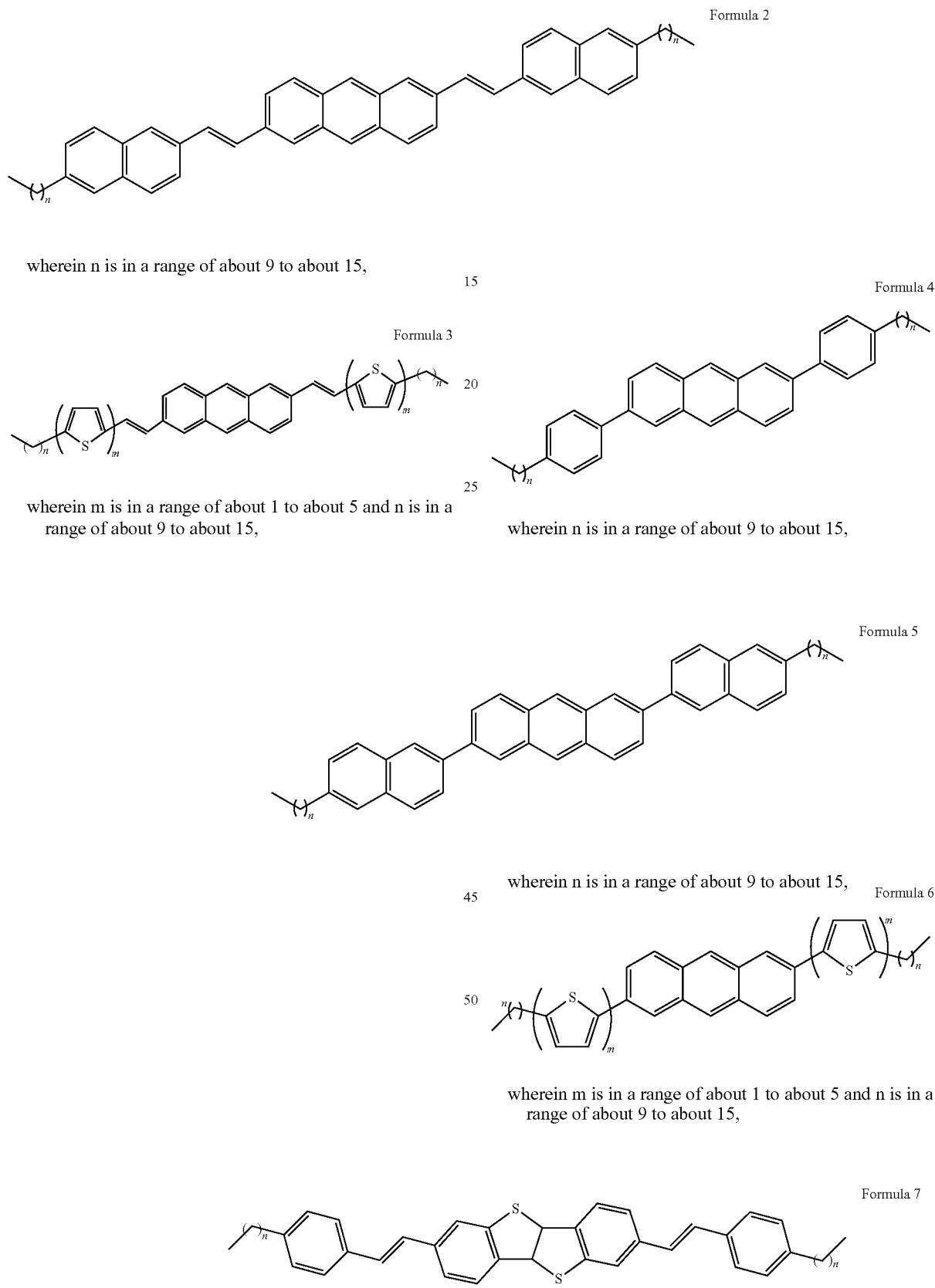
Formula 2
wherein n is in a range of about 9 to about 15,
Formula 3
wherein m is in a range of about 1 to about 5 and n is in a range of about 9 to about 15,
Formula 4
wherein n is in a range of about 9 to about 15,
Formula 5
wherein n is in a range of about 9 to about 15,
Formula 6
wherein m is in a range of about 1 to about 5 and n is in a range of about 9 to about 15,
Formula 7 wherein n is in a range of about 9 to about 15,

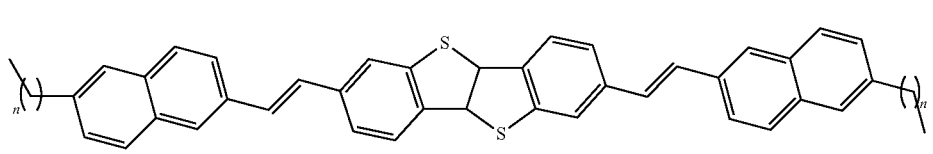

Formula 8 wherein n is in a range of about 9 to about 15,

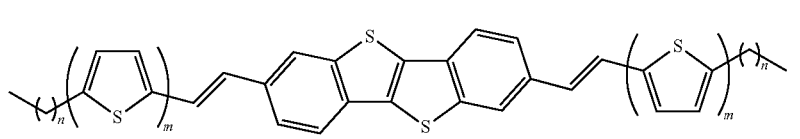

Formula 9 wherein m is in a range of about 1 to about 5 and n is in a range of about 9 to about 15, Formula 10

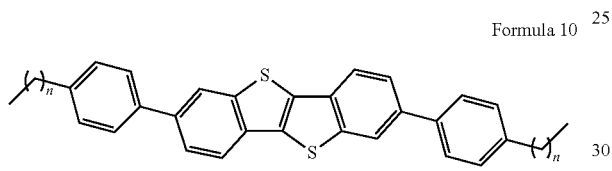

wherein n is in a range of about 9 to about 15,

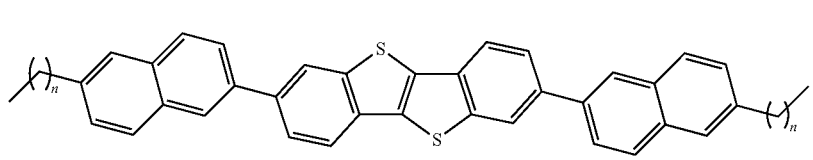

Formula 11 wherein n is in a range of about 9 to about 15, and

Formula 12

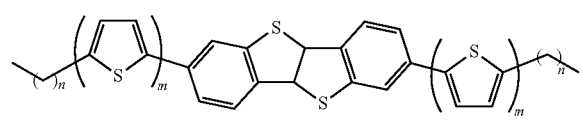

wherein m is in a range of about 1 to about 5 and n is in a range of about 9 to about 15.

6. The organic semiconductor transistor of claim 5, wherein the organic solvent comprises dimethyl sulfoxide.

* * * * *